United States Patent
Zhou et al.

(10) Patent No.: US 6,377,834 B1
(45) Date of Patent: Apr. 23, 2002

(54) REAL TIME IN VIVO MEASUREMENT OF TEMPERATURE CHANGES WITH CONTRAST ENHANCED NMR IMAGING

(75) Inventors: Yong Zhou, Waukesha, WI (US); Richard Frayne, Calgary (CA)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/557,263

(22) Filed: Apr. 24, 2000

Related U.S. Application Data

(60) Provisional application No. 60/134,916, filed on May 19, 1999.

(51) Int. Cl.⁷ .............................................. A61B 5/055
(52) U.S. Cl. ....................................... 600/412; 324/315
(58) Field of Search ........................ 600/412; 382/128; 424/9.3; 324/315, 307, 309

(56) References Cited

U.S. PATENT DOCUMENTS

| | | | |
|---|---|---|---|
| 4,558,279 A | * 12/1985 | Ackerman et al. | 324/300 |
| 5,207,222 A | * 5/1993 | Koizumi et al. | 324/315 |
| 5,323,779 A | * 6/1994 | Hardy et al. | 600/411 |
| 5,378,987 A | * 1/1995 | Ishihara et al. | 324/315 |
| 5,711,300 A | * 1/1998 | Schneider et al. | 600/412 |
| 5,713,358 A | 2/1998 | Mistretta et al. | 128/653.2 |
| 6,064,206 A | * 5/2000 | Van Vaals et al. | 324/309 |
| 6,067,371 A | * 5/2000 | Gouge et al. | 382/128 |
| 6,194,899 B1 | * 2/2001 | Ishihara et al. | 324/315 |

OTHER PUBLICATIONS

NMR Temperature Measurements Using a Paramagnetic Lanthanide Complex, JMR 133, 53–60 (1998), Article No. MN981429, Zuo et al.

Phase Imaging on a .2–T MR Scanner: Application to Temperature Monitoring During Ablation Procedures, JMRI 1997; 7:918–928, Sinha, et al.

Determination of the Intracellular Sodium Concentration in Perfused Mouse Liver by $^{31}$P and $^{23}$Na magnetic Resonance Spectroscopy, MRM 39:155–159 (1998), Colet, et al.

Magnetic Resonance Imaging of Temperature Changes During Interstitial Microwave Heating: A Phantom Study, Am. Assoc Phys. Med., 24(2), Feb. 1997, pp. 269–277, I.A. Vitkin, et al.

\* cited by examiner

*Primary Examiner*—Marvin M. Lateef
*Assistant Examiner*—Eleni Mantis Mercader
(74) *Attorney, Agent, or Firm*—Quarles & Brady, LLP

(57) ABSTRACT

NMR images indicative of thermal changes in tissues undergoing therapy are produced using a gradient-recalled echo pulse sequence. Prior to therapy a contrast agent which shortens spin $T_1$ relaxation time is injected into the patient and a reference phase image indicative of proton chemical shift is acquired. Temperature maps are produced in real-time as the therapy is subsequently performed by repeatedly acquiring NMR data, reconstructing measurement phase images and subtracting the reference phase image. The temporal rate at which the temperature maps are produced is increased by segmenting k-space and acquiring less than all the segments during each repetition.

12 Claims, 3 Drawing Sheets

REAL TIME IN VIVO MEASUREMENT OF TEMPERATURE CHANGES WITH CONTRAST ENHANCED NMR IMAGING

CROSS-REFERENCE TO RELATED APPLICATION

This application claims priority to U.S. provisional application No. 60/134,916, filed May 19, 1999, which is incorporated herein by reference as if fully set forth herein.

STATEMENT REGARDING FEDERALLY SPONSORED RESEARCH

This invention was made with United states Government support awarded by the following agencies: NIH Grant No. HL57501. The United States has certain rights in this invention.

BACKGROUND OF THE INVENTION

The field of the invention is nuclear magnetic resonance imaging (MRI) methods and systems. More particularly, the invention relates to the in vivo measurement of temperature changes using NMR imaging techniques.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

MR-guided interventional procedures employ the MRI system to produce real-time images which enable the procedure to be monitored. Such procedures, include MR-guided biopsies, hyperthermia, cryoablation, and ablation using laser, radiofrequency, and focused ultrasound. A critical part of such MR-guided ablation procedures is the ability to monitor spatially localized changes in temperature using heat-sensitive MR pulse sequences. Four different NMR properties of tissues have shown potential as parameters sensitive to temperature changes. These are the spin-lattice relaxation time T1, the molecular diffusion coefficient D, and the water proton chemical shift (PCS). The PCS method is based on the dependence of the water proton resonance frequency on temperature. Using this phenomenon, the phase of a gradient-echo image can be used to measure temperature as described, for example, in U.S. Pat. Nos. 5,307,812; 5,323,779; 5,327,884 and 5,711,300.

It has been shown that to achieve the optimal signal-to-noise ratio (SNR) in a temperature-sensitive phase image, the echo time (TE) of the pulse sequence used to acquire the NMR data should be equal to the spin-spin relaxation time constant $T_2^*$ of the imaged subject matter. The $T_2^*$ constant of tissues is typically on the order of 40 ms. As a result, a conventional scan can be quite long in duration if the TR period of the pulse sequence is set long enough to accommodate a 40 ms TE. In a 256×256 voyel 2D acquisition using pulse sequence with a TR=50 ms, for example, 13 seconds is required to acquire a complete 2D image data set. When a 3D temperature map is to be produced, the acquisition time becomes much longer and is not very useful in real-time imaging applications.

SUMMARY OF THE INVENTION

The present invention is a method for producing a temperature map which indicates the temperature of in vivo tissues or in vitro temperature calibration phantoms. More particularly, the present invention is a method in which an NMR contrast agent which alters the spin lattice relaxation time ($T_1$) of spins in the subject to be measured is applied to the subject, an NMR pulse sequence is performed with an MRI system to acquire an NMR data set from which an image may be reconstructed, and a phase image which indicates temperature is reconstructed from the NMR data. The NMR pulse sequence is continuously repeated to update the acquired NMR data such that temperature maps may be produced in real time to indicate temperature changes occurring during a medical procedure or the like. The temporal rate at which updated temperature maps are produced can be further increased by updating the NMR data set with central k-space samples at a higher rate than peripheral k-space samples are acquired.

A general object of the invention is to increase the temporal rate at which NMR temperature maps can be produced without reducing their SNR. It has been discovered that NMR contrast agents, such as Gd DPTA, enable the TE/TR period of a PCS sensitive NMR pulse sequence to be substantially reduced without diminishing the SNR of the resulting temperature map. This results in a shorter scan time and a consequent higher temperature map temporal rate. Importantly, it has been discovered that the temperature sensitivity of the NMR pulse sequence is not significantly altered by the contrast agent and the temperature measurement is not significantly affected by variations in contrast agent concentration.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
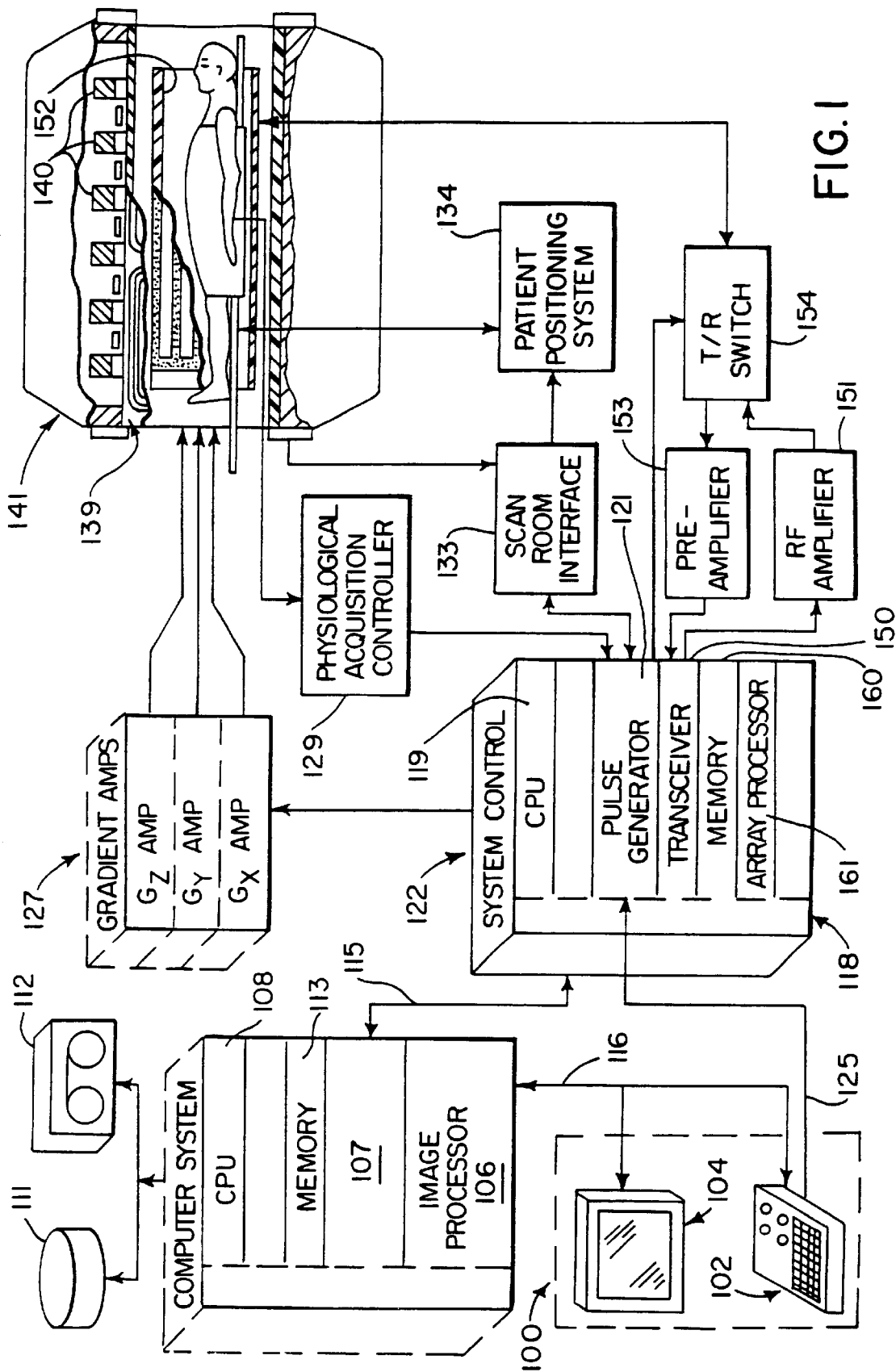
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane 118. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 112 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a wholebody RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

Figure 2:
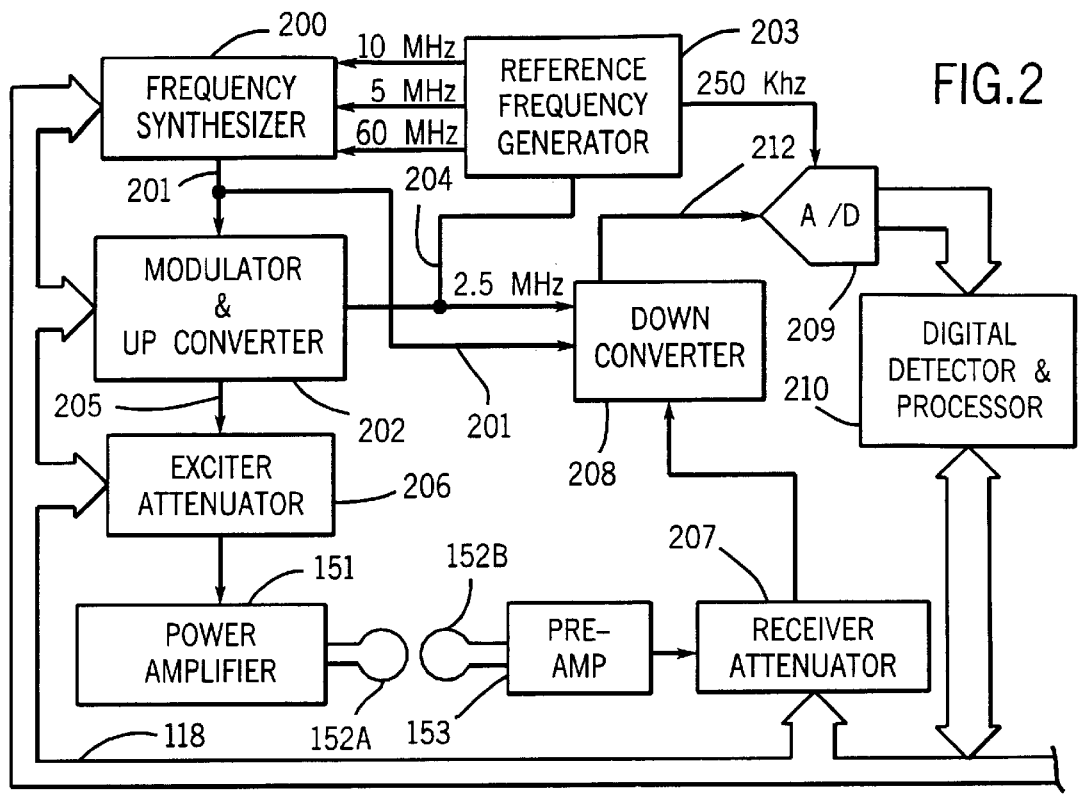
FIG. 2 is an electrical block diagram of the transceiver which forms part of the MRI system of FIG. 1.

Referring particularly to FIGS. 1 and 2, the transceiver 150 produces the RF excitation field B1 through power amplifier 151 at a coil 152A and receives the resulting signal induced in a coil 152B. As indicated above, the coils 152A and B may be separate as shown in FIG. 2, or they may be a single wholebody coil as shown in FIG. 1. The base, or carrier, frequency of the RF excitation field is produced under control of a frequency synthesizer 200 which receives a set of digital signals (CF) from the CPU module 119 and pulse generator module 121. These digital signals indicate the frequency and phase of the RF carrier signal produced at an output 201. The commanded RF carrier is applied to a modulator and up converter 202 where its amplitude is modulated in response to a signal R(t) also received from the pulse generator module 121. The signal R(t) defines the envelope of the RF excitation pulse to be produced and is produced in the module 121 by sequentially reading out a series of stored digital values. These stored digital values may, in turn, be changed from the operator console 100 to enable any desired RF pulse envelope to be produced.

The magnitude of the RF excitation pulse produced at output 205 is attenuated by an exciter attenuator circuit 206 which receives a digital command, TA, from the backplane 118. The attenuated RF excitation pulses are applied to the power amplifier 151 that drives the RF coil 152A. For a more detailed description of this portion of the transceiver 122, reference is made to U.S. Pat. No. 4,952,877 which is incorporated herein by reference.

Referring still to FIGS. 1 and 2 the signal produced by the subject is picked up by the receiver coil 152B and applied through the preamplifier 153 to the input of a receiver attenuator 207. The receiver attenuator 207 further amplifies the signal by an amount determined by a digital attenuation signal (RA) received from the backplane 118.

The received signal is at or around the Larmor frequency, and this high frequency signal is down converted in a two step process by a down converter 208 which first mixes the NMR signal with the carrier signal on line 201 and then mixes the resulting difference signal with the 2.5 MHz reference signal on line 204. The down converted NMR signal is applied to the input of an analog-to-digital (A/D) converter 209 which samples and digitizes the analog signal and applies it to a digital detector and signal processor 210 which produces 16-bit in-phase (I) values and 16-bit quadrature (Q) values corresponding to the received signal. The resulting stream of digitized I and Q values of the received signal are output through backplane 118 to the memory module 160 where they are employed to reconstruct an image.

The 2.5 MHz reference signal as well as the 250 kHz sampling signal and the 5, 10 and 60 MHz reference signals are produced by a reference frequency generator 203 from a common 20 MHz master clock signal. These provide a reference phase for the received NMR signals such that the phase is accurately reflected in the I and Q values. For a more detailed description of the receiver, reference is made to U.S. Pat. No. 4,992,736 which is incorporated herein by reference.

To practice the present invention a scan is performed using an imaging pulse sequence, and an image is reconstructed in which the phase information at each image pixel is preserved. A two-dimensional or a three-dimensional image pulse sequence may be employed, and a Fourier transformation is performed along each axis of the acquired array of complex signal samples. The phase at each image pixel may be calculated as the argument of the complex value at the pixel: $\phi=\tan^{-1}Q/I$. As will be described below, this phase measurement may be used to calculate a phase difference ($\Delta\phi$) at each image pixel which indicates tissue temperature change.

Figure 3:
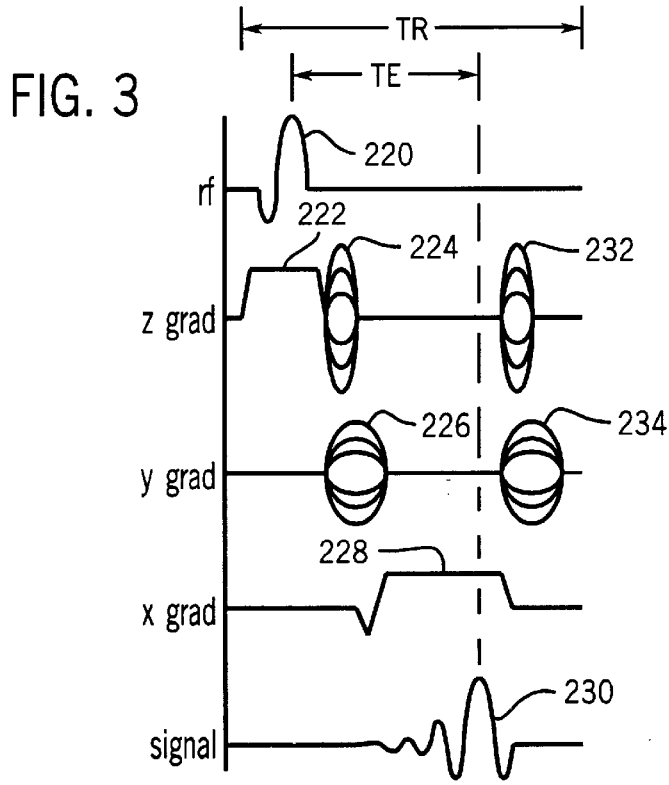
FIG. 3 is a graphic representation of a preferred pulse sequence used to acquire the phase image data according to the present invention.

In the preferred embodiment a gradient recalled echo pulse sequence is employed to acquire this phase image data. Referring particularly to FIG. 3, an RF excitation pulse 220 having a flip angle of 30° is produced in the presence of a slab select gradient pulse 222 to produce transverse magnetization in the 3D volume of interest as taught in U.S. Pat. No. 4,431,968. This is followed by a phase encoding gradient pulse 224 directed along the z axis and a phase encoding gradient pulse 226 directed along the y axis. A readout gradient pulse 228 directed along the x axis follows and a partial echo (60%) NMR signal 230 is acquired and digitized as described above. After the acquisition, rewinder gradient pulses 232 and 234 rephase the magnetization before the pulse sequence is repeated as taught in U.S. Pat. No. 4,665,365.

As is well known in the art, the pulse sequence is repeated and the phase encoding pulses 224 and 226 are stepped through a series of values to sample 3D k-space. In the preferred embodiment sixteen phase encodings are employed along the z axis. For each particular y phase encoding, therefore, sixteen acquisitions with sixteen different z phase encodings are performed to sample completely along the $k_z$ axis. This is repeated 80 times with 80 different y phase encodings to sample completely along the $k_y$ axis.

Sampling along the $k_x$ axis is performed by sampling the echo signal 230 in the presence of the readout gradient pulse 228 during each pulse sequence. Only a partial sampling of the echo signal 230 along the $k_x$ axis is performed and the missing data is computed using a homodyne reconstruction or by zero filling. The echo peak is located near the end of the acquisition window, which is contrary to the normal practice of locating the peak near the beginning of the acquisition window. This partial, asymmetric sampling of the echo signal 230 enables the echo time (TE) of the pulse sequence to be as long as possible within the pulse repetition rate (TR). This is contrary to prior asymmetric partial sampling methods which sample the echo peak early in the acquisition window to shorten the TE time. The echo time (TE) is further increased by decreasing the readout bandwidth (e.g. BW=3 kHz).

Tissue magnetic susceptibility changes as a function of temperature. This susceptibility change in turn causes spin resonance frequency shifts which vary linearly with temperature. For water the spin resonance frequency changes at a rate of approximately 0.01 ppm/° C. The resulting frequency shifts at three polarizing field strengths are set forth in Table 1.

TABLE 1

|  | $B_0 = 0.5$ T | $B_0 = 1.0$ T | $B_0 = 1.5$ T |
| --- | --- | --- | --- |
| Water Rate = 0.01 ppm/° C. | $\Delta v = 0.21$ Hz/° C. | $\Delta v = 0.42$ Hz/° C. | $\Delta v = 0.63$ Hz/° C. |

Typical temperature changes in tissues due to various therapies and procedures are set forth in Table 2.

TABLE 2

| Therapy | Temperature Change | Frequency Shift at 1.5 T |
| --- | --- | --- |
| Localization | 0–5° C. | 0–3.2 Hz |
| Focused Ultrasound | 23–63° C. | 14.5–40 Hz |
| Classic Hyperthermia | 8–13° C. | 5–8.2 Hz |

Thermally induced chemical shift changes can be sensitively monitored using phase images because the MR signal phase (proportional to frequency) shifts linearly as a function of temperature. For water spins (0.01 ppm/° C.), a relative 9.2 degree/° C. phase shift occurs at 1.5T for a 40 msec echo time (TE) in a gradient-recalled echo pulse sequence.

To produce a temperature map the pulse sequence of FIG. 3 is first used to acquire a reference phase image before the medical procedure is begun. The resulting 3D k-space data set ($I_R$, $Q_R$) provides a reference phase image that reflects not only the normal temperature of spins in the region of interest, but also phase shifts caused by other well-known factors. As will be described in more detail below, after the medical procedure to be monitored is started, additional 3D k-space data sets ($I_1$, $Q_1$) are acquired using the pulse sequence of FIG. 3. The information necessary to produce a temperature map is contained in the phase difference between the reference and measurement images. This information can be extracted in a number of ways. First, the phase difference ($\Delta\phi$) may be calculated at each image pixel $\Delta\phi=\tan^{-1}Q_R/I_R-\tan^{-1}Q_1/I_1$.

These phase difference values ($\Delta\phi$) are multiplied by a constant to produce numbers indicative of relative temperature. This is the preferred method when a quantitative temperature map is produced.

Figure 4:
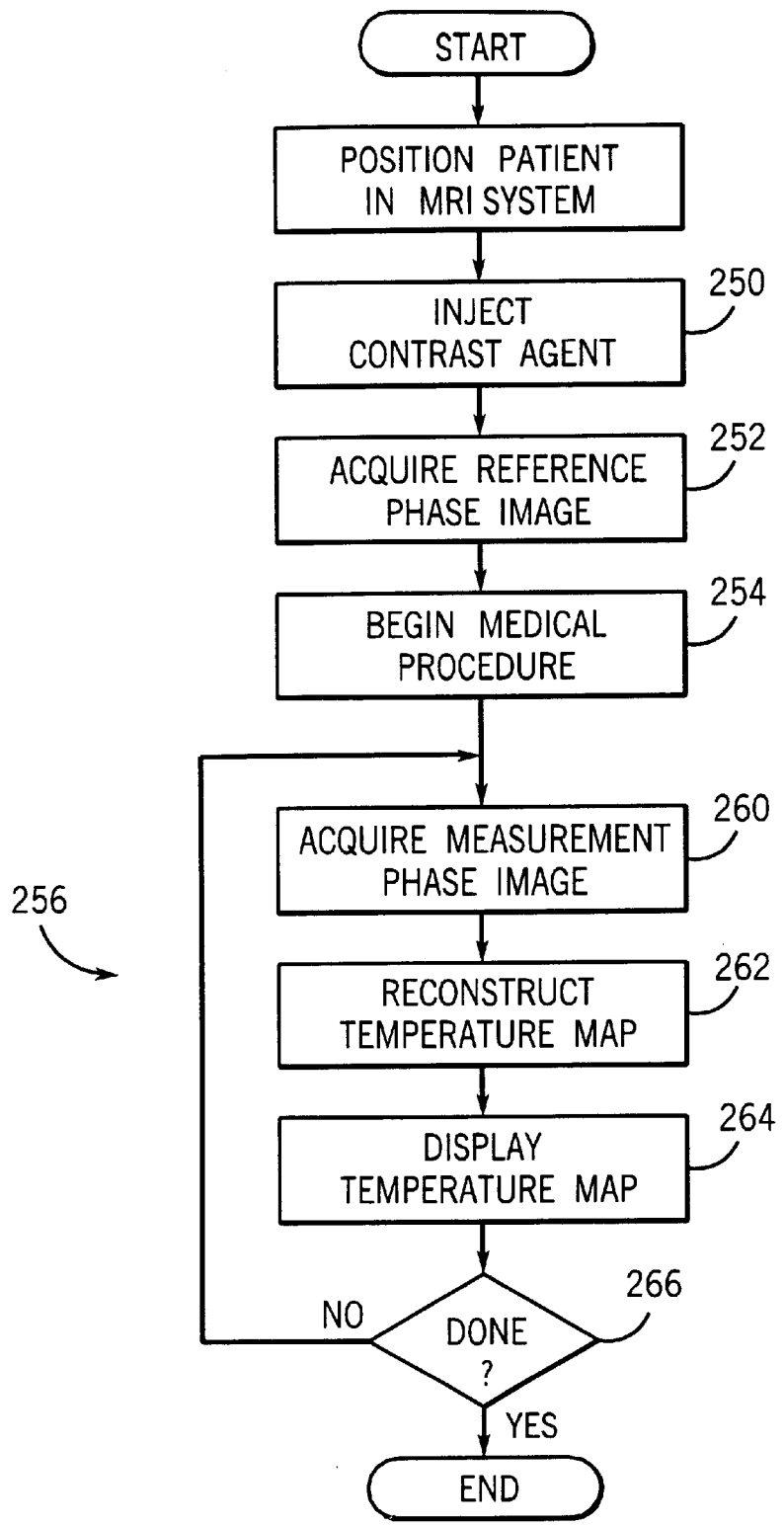
FIG. 4 is a flow chart of the steps used in the preferred embodiment of the invention.

While the present invention may be employed in many different situations, it has particular applicability to MR guided interventional procedures which involve heating of tissues in a patient. Referring to FIGS. 1 and 4, the patient is positioned in the bore of the MRI system magnet such that the anatomy of interest can be imaged. As indicated at block 250, the patient is then injected with an NMR contrast agent which travels through the patient's vasculature and permeates the anatomy of interest. In the preferred embodiment the contrast agent is Gd-DPTA manufactured by Nycomed of New York, N.Y. and sold under the trademark "OMNISCAN". Other contrast agents which function to shorten the $T_1$ spin-lattice relaxation time of the subject spins may also be used and the contrast agent may also be injected directly into the tissue subcutaneously.

As indicated at process block 252, after the contrast agent has permeated the subject tissues the reference phase image is acquired. As described above, the pulse sequence of FIG. 3 is used to acquire a complete k-space data set ($I_R$, $Q_R$) which provides the reference phase at each pixel in the reconstructed image. The medical procedure which is to be monitored can then be started, as indicated at process block 254. The system enters a loop indicated at 256 in which temperature maps of the subject anatomy are produced as rapidly as possible to provide the attending physician with real-time time feedback regarding the tissue heating which the procedure is producing. For example, if a thermal ablation device is used to ablate tissue at a particular location, the real-time three-dimensional temperature map indicates the temperature rise of the tissue at that location and in the surrounding region. The physician can thus observe that the proper tissue is being treated and that the temperature increase is sufficient to accomplish the desired result. In addition, the three-dimensional temperature map will indicate when the surrounding tissues are approaching an overheated condition and the ablation procedure should be terminated. To accomplish these goals it is important that the temperature map be updated at as high a temporal rate as possible. This is particularly true if 3D anatomic images are also being produced from the same NMR data to help guide the ablation device into the proper position.

Referring particularly to FIG. 4, after the medical procedure is started, the pulse sequence of FIG. 3 is employed as indicated at process block 260 to acquire k-space data ($I_1$, $Q_1$). During the first pass through the loop 256 a complete k-space NMR data set is acquired. However, k-space is divided into segments as described in U.S. Pat. No. 5,713,358 issued Feb. 3, 1998 and entitled "*Method For Producing A Time-Resolved Series Of 3D Magnetic Resonance Angiograms During The First Passage Of Contrast Agent*". In the preferred embodiment 3D k-space is divided into 8 segments (4 in $k_y$ direction and 2 in $k_z$ direction) and the segments closer to the origin of k-space (i.e. k=0) are sampled more frequently during subsequent passes through the loop 256. As indicated by process block 262, a temperature map is then reconstructed using the acquired 3D k-space data set. The updated k-space data is Fourier transformed along all three axes and the phase at each resulting pixel is calculated from the real (I) and imaginary (Q) components. The corresponding phase at each pixel in the reference phase image is subtracted to produce a temperature map that may be output directly to a display as indicated at process block 264. In this embodiment the brightness of each displayed image pixel is indicative of temperature difference at its corresponding voxel in the patient.

The temperature map produced in the preferred embodiment indicates the change in temperature between the time the reference phase image is acquired and the time the measurement phase image is acquired. An alternative embodiment is to measure the rate at which the temperature is increasing during the treatment procedure. In this case the reference phase image is updated at regular intervals during the treatment by using acquired measurement data. The temperature map in this embodiment indicates the temperature change since the last reference phase image update, or in other words, the rate at which the temperature is increasing during treatment.

In an alternative embodiment, a magnitude image is also produced from the image data set reconstructed from the acquired 3D k-space data set. The brightness of each pixel in this magnitude image is as follows:

$$M=\sqrt{I^2+Q^2}.$$

The temperature values indicated by the temperature map are combined with this magnitude image by modulating the color of each corresponding pixel therein. Cooler temperatures are indicated by blue and the hottest temperatures are indicated by yellow. This color modulation of the magnitude image provides the physician with an anatomic image that clearly shows the anatomy being treated and the location and orientation of the medical device used to perform the treatment. The color of the anatomic structures indicates their temperature. The temperature desired for treatment may also be input and used as a threshold that produces a specific color (e.g. red) on the temperature map. That is, tissues which reach this threshold temperature are displayed red on the temperature map.

As indicated at by the decision block 266, the system remains in the loop 256 until the medical procedure is completed. As indicated above, during subsequent passes through the loop 256 the 3D k-space data set is only partially updated by acquiring two of the eight defined k-space segments. During each pass the central-most k-space segment is sampled along with two of the other seven "peripheral" segments. The rate at which the peripheral segments are updated is a function of their distance from the center of k-space as described, for example, in the above-cited U.S. Pat. No. 5,713,358. It has been discovered that temperature variations throughout the image have low spatial frequency components and that only the central most segment of k-space need be sampled to accurately depict these variations. Thus, a substantial increase in temporal resolution may be achieved by acquiring only three of the eight segments without sacrificing temperature image resolution. By sampling the remaining peripheral segments during the procedure, however, the details of the anatomic image are also updated at a reasonable rate.

A rapid, high spatial and high temperature resolution in vivo temperature mapping technique has been presented. While a gradient-recalled echo pulse sequence is used to produce the phase images in the preferred embodiment, other well-known imaging pulse sequences can be used. Spin echo pulse sequences can also be used, and either 2D or 3D pulse sequences will work.

We claim:

1. A method for producing an image indicative of temperature changes in a subject positioned in an MRI system, the steps comprising a) altering the spin lattice relaxation time ($T_1$) of spins in the tissues in the subject;

b) performing an NMR pulse sequence to acquire reference NMR data from tissues in the subject;

c) reconstructing a reference phase image from the acquired NMR data d) performing an NMR pulse sequence to acquire measurement NMR data from said tissues;

e) reconstructing a measurement phase image from the acquired measurement NMR data; and f) producing a temperature map based on the difference between the measurement phase image and the reference phase image.

2. The method as recited in claim 1 in which a scan is performed by repeating steps d), e) and f) a plurality of times to produce a corresponding plurality of additional temperature maps.

3. The method as recited in claim 2 in which the measurement NMR data is comprised of a plurality of k-space segments, and less than all the k-space segments are acquired during each repeat of steps d), e) and f).

4. The method as recited in claim 2 which includes periodically updating the reference phase image using measurement NMR data acquired during the scan.

5. The method as recited in claim 4 in which the temperature maps indicate the rate at which temperature is increasing during the scan.

6. The method as recited in claim 1 in which the NMR pulse sequences are gradient echo pulse sequences.

7. The method as recited in claim 1 in which the temperature map is produced by calculating the phase difference between corresponding values in the measurement phase image and the reference phase image.

8. The method as recited in claim 1 in which step a) is performed by injecting a contrast agent into the subject.

9. The method as recited in claim 8 in which the contrast agent is Gd-DPTA.

10. The method as recited in claim 1 in which the NMR pulse sequences are three-dimensional gradient echo pulse sequences and the reference phase image, the measurement phase image and the temperature map are three-dimensional.

11. The method as recited in claim 10 in which the NMR data acquired with the NMR pulse sequences is a partial gradient echo signal in which the echo peak is nearer the end of an acquisition window in each NMR pulse sequence.

12. The method as recited in claim 11 in which the partial gradient echo signal is acquired with a minimum readout bandwidth.

\* \* \* \* \*